(12) United States Patent
Kahn et al.

(10) Patent No.: US 7,252,638 B2
(45) Date of Patent: Aug. 7, 2007

(54) METHOD AND SYSTEM FOR SIMULTANEOUSLY DISPLAYING RELATIONSHIPS OF MEASUREMENTS OF FEATURES ASSOCIATED WITH A MEDICAL IMAGE

(75) Inventors: Robert D. Kahn, Saratoga, CA (US); Edward A. Gardner, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 180 days.

(21) Appl. No.: 10/601,413

(22) Filed: Jun. 23, 2003

(65) Prior Publication Data

US 2004/0260178 A1    Dec. 23, 2004

(51) Int. Cl.
   *A61B 8/00*    (2006.01)
(52) U.S. Cl. ..................................... 600/443
(58) Field of Classification Search ............... 600/437, 600/438, 440, 443–447, 449–450, 453–456; 128/916; 382/128, 131
   See application file for complete search history.

(56) References Cited

U.S. PATENT DOCUMENTS

| | | | | | |
|---|---|---|---|---|---|
| 3,922,911 | A | * | 12/1975 | Groves et al. | 73/861.25 |
| 5,337,752 | A | * | 8/1994 | Reeves | 600/513 |
| 5,343,867 | A | * | 9/1994 | Shankar | 600/481 |
| 5,701,897 | A | * | 12/1997 | Sano | 600/453 |
| 6,058,322 | A | * | 5/2000 | Nishikawa et al. | 600/408 |
| 6,198,797 | B1 | * | 3/2001 | Majima et al. | 378/98 |
| 6,205,348 | B1 | * | 3/2001 | Giger et al. | 600/407 |
| 6,213,945 | B1 | | 4/2001 | Tynan | |
| 6,273,854 | B1 | * | 8/2001 | Kane et al. | 600/300 |
| 6,464,640 | B1 | * | 10/2002 | Guracar et al. | 600/453 |
| 6,571,003 | B1 | * | 5/2003 | Hillebrand et al. | 382/118 |
| 6,811,536 | B2 | * | 11/2004 | Sun et al. | 600/500 |

OTHER PUBLICATIONS

Hadlock, F. et. al., "Fetal Crown-Rump Length: Reevaluation of Relation to Menstrual Age (5-18 weeks) with High-Resolution Real-Time US," Radiology, vol. 182, No. 2, pp. 501-505, Feb. 1992.
"Ultrasound Online CME Courses—Fetal Intrauterine Growth Restriction (IUGR)," www.gemedicalsystems.com/inen/rad/us/education/msucmeiu.html, 10 pages (printed May 27, 2003).
"Estimation of Fetal Weight," www.emedicine.com/med/topic3281.htm, 24 pages (Jul. 11, 2002).
"About the Gestational Age Calculator," www.med.upenn.edu/fetus/calcinfo.html, 1 page (1988).

(Continued)

*Primary Examiner*—Francis J. Jaworski

(57) ABSTRACT

The embodiments described herein relate to a method and system for simultaneously displaying relationships of measurements of features associated with a medical image. In one embodiment, a plurality of measurements of features associated with a medical image are provided. Each of the plurality of measurements corresponds to a respective measurement type. Relationships are created between the measurements and references specific to the measurement types, and at least two of the created relationships are simultaneously displayed in a graphical display format. Examples using fetal growth data and time intensity curves are disclosed. Other embodiments are provided, and each of the embodiments described herein can be used alone or in combination with one another.

16 Claims, 3 Drawing Sheets

OTHER PUBLICATIONS

"OB-Gyn Ultrasound FAQ's," www.womensclinicseattle.com/ultrasound.htm, 4 pages (printed May 27, 2003).

Hadlock, F. et. al., "Estimating Fetal Age: Computer-Assisted Analysis of Multiple Fetal Growth Parameters", Radiology, vol. 152, No. 2, pp. 497-501, Aug. 1984.

Chitty, L. et. al., "Charts of fetal size: 2. Head measurements", British Journal of Obstetrics and Gynaecology, vol. 101. pp. 35-43, Jan. 1994.

Chitty, et. al., "Charts of fetal size: 3. Abdominal measurements", British Journal of Obstetrics and Gynaecology, vol. 101, pp. 1-7, Feb. 1994.

Chitty, et. al., "Charts of fetal size: 4. Femur length", British Journal of Obstetrics and Gynaecology, vol. 101, pp. 132-135, Feb. 1994.

Hellman, L., et. al., "Growth and development of the human fetus prior to the twentieth week of gestation", Am. J. Obst. & Gynec., vol. 103, No. 6, pp. 789-800, Mar. 15, 1969.

Goldstein, I., et. al., "Cerebellar measurements with ultrasonography in the evaluation of fetal growth and development", Am. J. Obst & Gynec., vol. 156, No. 5, pp. 1065-1069, May 1987.

Hata, T. and R. Deter, "A Review of Fetal Organ Measurements Obtained with Ultrasound: Normal Growth", J. Clin. Ultrasound 210:155-174, Mar./Apr. 1992.

Jeanty, P. et. al., "Estimation of Gestational Age from Measurements of Fetal Long Bones", Journal of Ultrasound in Medicine, vol. 3, pp. 75-83, Feb. 1984.

Gardner et al., "Synchronization of Contrast Agent Destruction and Imaging for Perfusion Assessment," 2000 IEEE Ultrasonics Symposium, pp. 1911 and 1914 (2000).

Fernandez et al., "Practica de la Ecocardiografia de Contraste," Cuantificacion de la Perfusion Miocardica Mediante Ecocardiografia de Contraste: Bases Metodologicas, pp. 98-99 (1999).

"HDI 3000 Ultrasound System Reference Manual," pp. 13-91 and 13-92 (1997).

"Sequoia Ultrasound System User Manual," Document No. 58092, Rev. 1, pp. 115-119 (1999).

"Formulas and Calculations," http://www.echobyweb.com/htm_level2_eng/formulas&calculations.htm, 4 pages (printed Jun. 6, 2003).

Shinozuka et al., "Formulas for Fetal Weight Estimation by Ultrasound Measurements Based on Neonatal Specific Gravities and Volumes," American Journal of Obstetrics and Gynecology, pp. 1140-1145 (1987).

Wei et al, "Basis for Detection of Stenosis Using Venous Administration of Microbubbles during Myocardial Contrast Echocardiography: Bolus or Continuous Infusion," Am Coll Cardiol 32:252-60 (1998).

Linka et al., "Assessment of Transmural Distribution of Myocardial Perfusion with Contrast Echocardiography," Circulation 98: 1912-1920 (1998).

* cited by examiner

METHOD AND SYSTEM FOR SIMULTANEOUSLY DISPLAYING RELATIONSHIPS OF MEASUREMENTS OF FEATURES ASSOCIATED WITH A MEDICAL IMAGE

BACKGROUND

Some of the objectives of an obstetric ultrasound examination are to determine whether the growth of a fetus is consistent with a best estimate of the fetus' age and to determine whether the relative sizes of various anatomical components are in correct proportion. To support these objectives, medical diagnostic ultrasound imaging systems can display fetal growth data in the form of "growth curves," which depict the expected size of a component of fetal anatomy as a function of gestational age. FIG. 7 is an example of a conventional fetal growth curve showing biparietal diameter (BPD) as a function of gestational age (GA) over the course of a gestation. As shown in FIG. 7, the growth curve comprises three distinct plotted curves: one representing the mean or expected biparietal diameter for a given gestational age (curve 1), and two other curves above and below the mean showing the normal statistical variation to be found among healthy fetuses (curves 2 and 3). The growth curve also shows a data point (X), which is the biparietal diameter measurement acquired during an ultrasound examination of a patient. A sonographer or physician makes a determination regarding the status of the fetus by looking at the growth curve to determine whether the measured anatomy lies within a normal range.

Separate growth curves are generated for different types (or "dimensions") of fetal growth data, and each of these growth curves are examined to obtain a global picture of the normalcy of the fetus' growth. Because growth curves only show a single dimension of fetal growth data and current ultrasound systems and image review systems only display a single growth curve at any given time, a sonographer or physician must page through a sequence of growth curves to diagnose the fetus', growth. This sequential analysis of growth curves introduces a risk of a missed diagnosis since a key growth curve can easily be overlooked. Similar problems can occur with other measurements of features associated with a medical image.

SUMMARY

The present invention is defined by the following claims, and nothing in this section should be taken as a limitation on those claims.

By way of introduction, the embodiments described herein relate to a method and system for simultaneously displaying relationships of measurements of features associated with a medical image. In one embodiment, a plurality of measurements of features associated with a medical image are provided. Each of the plurality of measurements corresponds to a respective measurement type. Relationships are created between the measurements and references specific to the measurement types, and at least two of the created relationships are simultaneously displayed in a graphical display format. Examples using fetal growth data and time intensity curves are disclosed. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

Introduction

Figure 1:
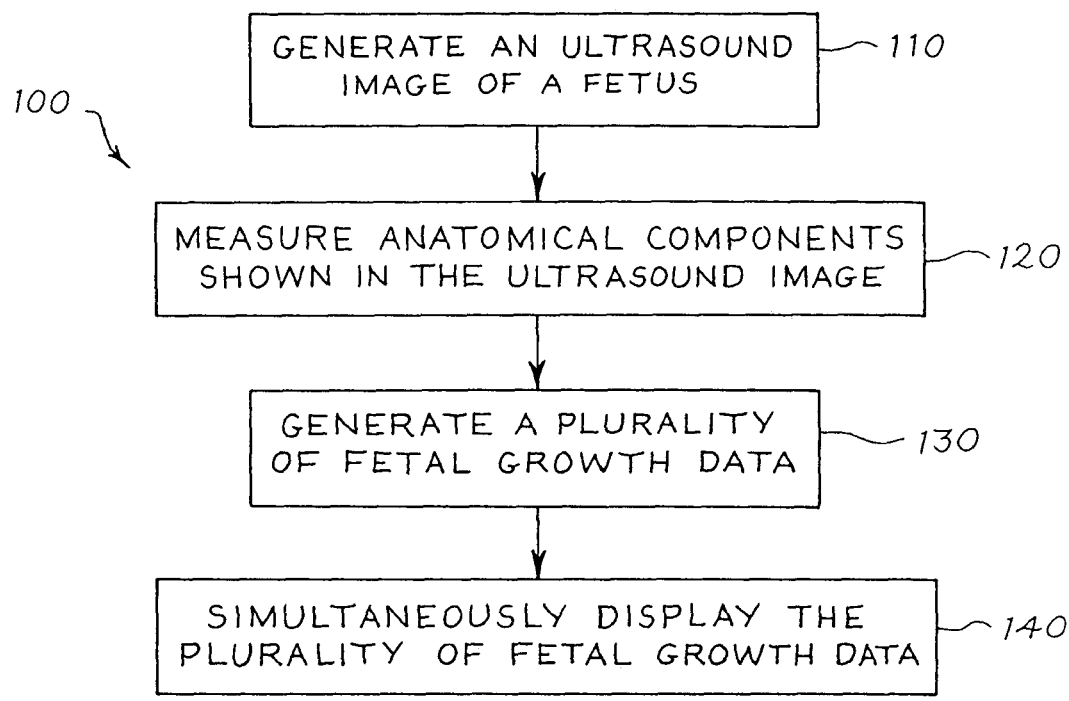
FIG. 1 is a flow chart of a method of an embodiment for simultaneously displaying fetal growth data.

In general, the embodiments described below can be used to simultaneously display relationships of measurements of features associated with a medical image. In operation, a plurality of measurements of features associated with a medical image are provided. Each of the plurality of measurements corresponds to a respective measurement type. For each of the plurality of measurements, a relationship between the measurement and the reference specific to its measurement type is created. Then, at least two of the created relationships are simultaneously displayed in a graphical display format.

A "measurement of a feature associated with a medical image" can be any quantification of a physiological attribute that (a) appears directly in a medical image (e.g., the diameter of a heart chamber), (b) is a calculation derived from raw imaging data (e.g., a calculation of Resistance Index), or (c) is available through the imaging system even though it is not data that is used to create a medical image (e.g., heart-rate made available to the imaging system via an EKG which plugs into the imaging system). The following is a list of examples of various measurements of features. This list is not comprehensive, and other measurements can be made, such as those listed at http://www.echobyweb.com/htm_level2_eng/formulas&calculations.htm.

Tumor diameter/area/volume.

Various organ and organ component diameters/areas/volumes.

Blood flow velocity through various significant vessels, for example, different sites on the Carotid Arteries, the Pulmonary Vein, the Aorta, Hepatic vessels, renal arteries, blood vessels in the legs.

Resistance index (RI) of blood flow through a vessel, where RI is defined as $|Vmax-Vmin|/\max(|Vmax|, |Vmin|)$, where Vmax is the systolic velocity and Vmin is the diastolic velocity measured during a heart cycle.

Time-Averaged-Velocity (TAV) of blood flow through a vessel. This is the average flow velocity over a set span of time.

Pulsitility index (PI) of blood flow through a vessel, where PI is defined as $|Vmax-Vmin|/TAMx$, where Vmax is the systolic velocity, Vmin is the minium diastolic velocity, and TAMx is the maximum velocity averaged over (at least) one cardiac cycle.

Ratio of blood velocity at systole and diastole.

Vascular Stenosis, which is the percent blockage of a blood vessel, calculated from measurements of the vessel's outer diameter and inner diameter, or alternatively the outer cross-sectional area and inner cross-sectional area.

Ejection Fraction, which is the proportion of blood pumped out of the heart with each beat, computed from measuring the percentage change in heart chamber volumes between systole and diastole.

Wash-in and wash-out rates.

The measurements have normal ranges and ranges outside the norm, which are indicative of some kind of pathology. Given that there is an expected "normal" value (e.g., an average value found among a healthy population) and an expected standard deviation away from "normal" found among healthy persons, then any measurement can be expressed in a unitless (normalized) way by using the following equation: NormalizedMeasurementValue=(Measured Value–"Normal" Value)/StandardDeviation. The NormalizedMeasurementValue is then simply the number of standard deviations away from "Normal." Because any measurement can be normalized in this way, regardless of the measurement (whether it be a distance, a volume, a flow velocity, etc), it is possible to meaningfully display diverse measurements on the same x-y plot, where the vertical (y) axis is the unitless measure of deviation (measured in standard deviations) from normal and where the horizontal (x) axis is the plurality of measurements of features associated with a medical image.

As discussed above, each of the plurality of measurements corresponds to a respective measurement type, and each of the plurality of measurements is associated with a reference specific to its measurement type. If all of the measurements correspond to the same measurement type, all of the measurements can be compared to the same reference. Otherwise, each measurement can be normalized to an appropriate reference specific to that measurement type. Then, all the normalized measurements can be displayed together to provide a meaningful comparison of the different measurements relative to "normal." This makes it possible to simultaneously display measurements of diverse nature, for example, a heart rate (bpm), a flow velocity (m/s), and a wall thickness (mm). Each of these is measured in different units, but they all have expected ranges (e.g., an average value for healthy patients, and a standard deviation to be found among healthy patients). By normalizing each measurement relative to its expected range (e.g., how many standard deviations away from average is it?), all the measurements are simultaneously displayable in a single plot. Simultaneously displaying these relationships in a graphical display format can be used to assist a user diagnose a healthy or unhealthy condition. Various types of measurements can be simultaneously displayed, and the choice of which types to simultaneously display can be made by a user.

The following examples illustrate the embodiments described above as applied to fetal growth data and time intensity curves. It is important to note that these embodiments can be used in other applications and that the following claims should not be limited to fetal growth data or time intensity curves unless explicitly recited therein.

Example Using Fetal Growth Data

Figure 2:
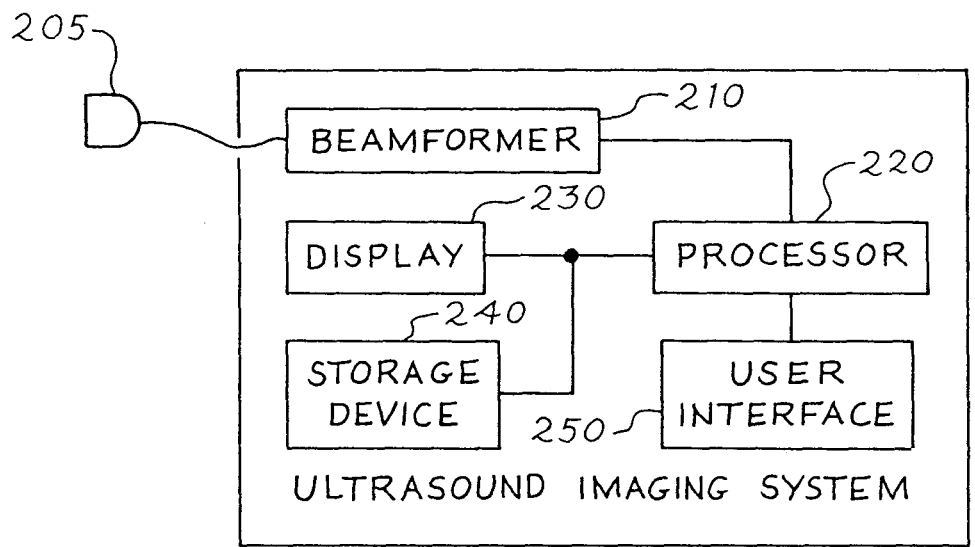
FIG. 2 is a block diagram of a medical diagnostic ultrasound imaging system of an embodiment.

One application of the general technique described above relates to fetal growth data and will be described in conjunction with the flow chart 100 of FIG. 1. As shown in FIG. 1, a medical diagnostic ultrasound image of a fetus is generated with a medical diagnostic ultrasound imaging system (act 110), such as the medical diagnostic ultrasound imaging system 200 illustrated in FIG. 2. As shown in FIG. 2, the ultrasound system 200 comprises a transducer probe 205, a beamformer 210, a processor 220, a display device 230, a storage device 240, and a user interface 250. Some or all of the functionality described herein can be performed by the processor 220 running software (i.e., computer-readable program code) stored in the storage device 240 or some other location not shown. Alternatively, some or all of the functionality described herein can be implemented purely with hardware (e.g., with the processor 220 alone and/or with other hardware component(s) not shown). The hardware/software components can take any suitable form. Further, the ultrasound system 200 can comprise additional components, Which are not shown in FIG. 2 for simplicity. For example, although only a single processor 220 is shown in FIG. 2, it should be understood that the ultrasound system 200 can comprise multiple processors and that the functionality described herein can be performed by a single processor or can be distributed among several processors.

During an obstetrics ultrasound examination, a sonographer contacts the transducer probe 205 with a patient, and the ultrasound system 200 generates an ultrasound image of a fetus. In general, the ultrasound system's processor 220 causes the beamformer 210 to apply a voltage to the transducer 205 to cause it to vibrate and emit an ultrasonic beam into the portion of the patient's body in contact with the transducer 205. Ultrasonic energy reflected from the patient's body impinges on the transducer 205, and the resulting voltages created by the transducer 205 are received by the beamformer 210. The processor 220 processes the sensed voltages to create an ultrasound image and displays the image on the display device 230. In addition to being displayed on the display device 230, a generated ultrasound image can also be stored in digital form in the storage device 240 for later review. Images can also be transferred to removable media (e.g., a magneto-optical disk) or sent over a network (e.g., a local area network in a hospital or the Internet).

Once the ultrasound image is displayed on the display device 230, the sonographer measures anatomical components shown in the displayed ultrasound image using displayed measurement tools that are manipulated with the user interface 250 (act 120). Based on the measurements of the anatomical components, a plurality of fetal growth data is generated (act 130). As used herein, the term "fetal growth data" broadly refers to any data that is generated based on a measurement of an anatomical component shown in a medical image and that can be used to assess the growth of a fetus. As also used herein, fetal growth data is "based on" a measurement when the fetal growth data is the measurement itself or is the result of a calculation using the measurement.

The following are some examples of fetal growth data. It should be understood that the term "fetal growth data" as used in the claims is not limited to the following examples and that other forms of fetal growth data can be used. Information about these and other fetal biometry measurements can be found at the following sources, each of which is hereby incorporated by reference.

Hadlock, F. et. al., "Fetal Crown-Rump Length: Reevaluation of Relation to Menstrual Age (5-18 weeks) with High-Resolution Real-Time US," Radiology, vol. 182, no. 2, pages 501-505, February 1992;

Hadlock, F. et. al., "Estimating Fetal Age: Computer-Assisted Analysis of Multiple Fetal Growth Parameters", Radiology, vol 152, no. 2, pages 497-501, August 1984.

Chitty, L. et. al., "Charts of fetal size: 2. Head measurements", British Journal of Obstetrics and Gynaecology, vol 101. pp 35-43, January 1994.

Chitty, et. al., "Charts of fetal size: 3. Abdominal measurements", British Journal of Obstetrics and Gynaecology, vol. 101, pp.1-7, February 1994.

Chitty, et. al., "Charts of fetal size: 4. Femur length", British Journal of Obstetrics and Gynaecology, vol. 101, pp.132-135, February 1994.

Hellman, L., et. al., "Growth and development of the human fetus prior to the twentieth week of gestation", Am. J. Obst. & Gynec., Volume 103, no. 6, pp. 789-800, Mar. 15, 1969.

Goldstein, I., et. al., "Cerebellar measurements with ultrasonography in the evaluation of fetal growth and development", Am. J. Obst & Gynec., Volumne 156, No. 5, pp 1065-1069, May 1987.

Hata, T. and R. Deter, "A Review of Fetal Organ Measurements Obtained with Ultrasound: Normal Growth", J. Clin. Ultrasound 210:155-174, March/April 1992.

Jeanty, P. et. al., "Estimation of Gestational Age from Measurements of Fetal Long Bones", Journal of Ultrasound in Medicine, Volume 3, pp. 75-83, February 1984.

Biparietal Diameter (BPD)

The biparietal diameter is the transverse width of the head measured between the two sides of the head. The biparietal diameter can be used to calculate gestational age.

Head Circumference (HC)

The circumference of the fetus' head can be used to calculate gestational age with a degree of accuracy that is slightly better than that derived from the biparietal diameter.

Abdominal Circumference (AC)

Abdominal circumference is measured at the widest point in the abdomen, through the liver at the level of the left portal vein or stomach. Abdominal circumference is determined not only by growing tissues (mainly liver) but also by nutrient storage such as subcutaneous fat and liver glycogen. Serial measurements of the abdominal circumference are useful in monitoring the growth of the fetus.

Femur Length (FL)

The femur length measurement measures the longest bone in the body and reflects the longitudinal growth of the fetus. Its usefulness is similar to that of the biparietal diameter measurement. Accuracy of gestational age from femur length measurements is relatively independent of nutritional-growth retarding processes.

Crown Rump Length (CRL)

The crown rump length measurement can be made between 7 to 13 weeks and gives an accurate estimation of the gestational age. The crown rump length measurement is an early standard of reference for fetal dating with ultrasound and is useful in the first trimester of pregnancy Estimated Fetal Weight (EFW)

Sonographic prediction algorithms use various combinations of abdominal circumference (AC), femur length (FL), biparietal diameter (BPD), and head circumference (HC), both singly and in combination, to make fetal weight estimations.

Intracranial Organs

Ratio of the Cerebellum's Lateral Ventricular Width to the Hemispheric Width (LVW/HW).

Cerebroatrial distance (CAD).

Ratio of the cerebroatrial distance (CAD) to hemispheric width (HW).

Posterior Horn Width (PHW), measured from the medial wall to the lateral wall of the posterior horn of the lateral ventricle.

Cerebroposterior horn distance (CPHD), measured from the medial wall to the lateral wall of the posterior horn of the lateral ventricle.

Transverse cerebellar diameter (TCD).

Heart

Left ventricular transverse diameter (LVTD).
Right ventricular transverse diameter (RVTD).
Aortic diameter (AOD).
Pulmonary artery diameter (PAD).

Lung

Left lung circumference (LLC).
Right lung circumference (RLC).
Lung Area (LA) in a transverse section of the fetal thorax containing the four-chamber view of the heart.

Thymus

Maximal Anterior-posterior diameter (APD) of the thymus, measured in the midline at the sternum.

Liver

Liver Length (LL).

Spleen

Spleen Length (SL).
Spleen Width (SW).
Spleen Area (SA).

Pancreas

Length of fetal pancreas (FP-L).

Stomach

Longitudinal and anteroposterior diameters of the stomach.

Kidney

Anteroposterior Diameter.
Transverse Diameter.
Length.
Circumference.
Area.
Volume.

Adrenal Gland

Fetal adrenal gland area (FAGA).
Fetal adrenal gland length (FAGL).
Fetal adrenal gland circumference (FAGC).

Intestine

Colon diameter (CD).

Bladder

Maximum bladder volume (MBV).
Fetal urine production rate (FUPR).

Misc.

Anterior-posterior trunk/thorax diameter (APTD).
Transverse trunk diameter (TTD).
Spine length (SL).

As mentioned in the background section above, different dimensions of fetal growth data are typically displayed as separate growth curves, with only one growth curve being displayed at a given time. Because the sonographer must page through a sequence of growth curves to obtain a global picture of the normalcy of the fetus' growth, the sonographer can overlook an important growth curve. To remove this risk, this embodiment simultaneously displays the plurality of generated fetal growth data in a graphical format (act 140). The plurality of fetal growth data is "simultaneously displayed" when all of the plurality of fetal growth data is presented at a given time to a user for viewing, even if a delay prevents all of the fetal growth data from being initially displayed exactly at the same instant. The term "simultaneously display" is intended to distinguish from the sequential display of fetal growth data, which occurs when a user pages through a sequence of individual fetal growth curves to cause the display of one fetal growth curve to be replaced by the display of a different fetal growth curve. The plurality of fetal growth data can be simultaneously displayed on a single display device or across multiple display devices and can be presented in a single graph or in multiple graphs. Further, while the phrase "graphical display format" is intended to distinguish from a mere listing of numerical data (e.g., a tabular chart of numerical values of fetal growth data), no limit is intended on the form of the graphical format. Additionally, it should be noted that the graphical display format can include elements in addition to the various dimensions of fetal growth data, such as an image or a chart of numbers.

Figure 3:
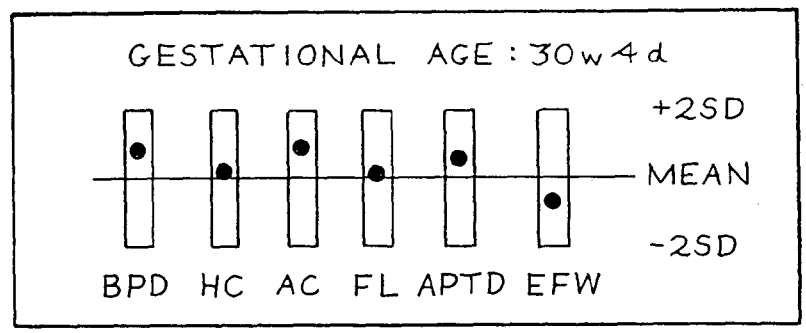
FIG. 3 is an illustration of a graphical display format of an embodiment.

Turning again to the drawings, FIG. 3 is an example of a graphical display format of an embodiment that can be used to simultaneously display fetal growth data. In the embodiment shown in FIG. 3, six different dimensions of fetal growth data are simultaneously displayed in a graphical format on a single page. In this embodiment, each dimension is represented by a bar on a graph, and abbreviations for each dimension of fetal growth data appear along the bottom of the graph. Above each measurement name is a bar, normalized so that the midpoint of the bar represents the expected value (mean) of the physiology represented by the fetal growth data, given the current estimate of the fetus' gestational age, which is 30 weeks, 4 days in this example. The upper and lower extents of each bar are normalized to represent the standard deviations expected in the measurement of the physiology for a normal fetus. Dots indicate measurements obtained during the examination, and dots lying outside the normal range can be color-coded for emphasis. If closer examination is required of a particular dimension (e.g., BPD), the bar representing that dimension can be selected using a user interface device and expanded into a traditional growth curve plot.

In contrast to conventional display techniques in which each dimension of fetal growth data is displayed on its own graph separate from all other anatomical data, the display format of this embodiment provides an improved mechanism for rapid determination of the normalcy of the current fetal state by simultaneously displaying several components of fetal growth data. In this embodiment, values and standard deviations of several anatomic measurements made during an examination are graphically displayed side-by-side so that multiple dimensions of fetal growth data can be quickly evaluated by a physician or sonographer. Because this display format simultaneously displays multiple dimensions of fetal growth data, a physician or sonographer can establish whether the fetus is developing normally in a single glance. Providing a multidimensional view of fetal growth data can significantly decrease the likelihood that an important aspect of the fetal physiology will be overlooked and, thus, reduce the possibility of an inaccurate diagnosis or a misdiagnosis of fetal pathology. By allowing all aspects of fetal development to be easily assessed by examination of a single graph that presents all of the fetal growth data in an easy-to-read format, the multidimensional display format of this embodiment overcomes the disadvantages of existing growth curve presentation techniques by providing a superior perspective on all dimensions of fetal growth.

Figure 4:
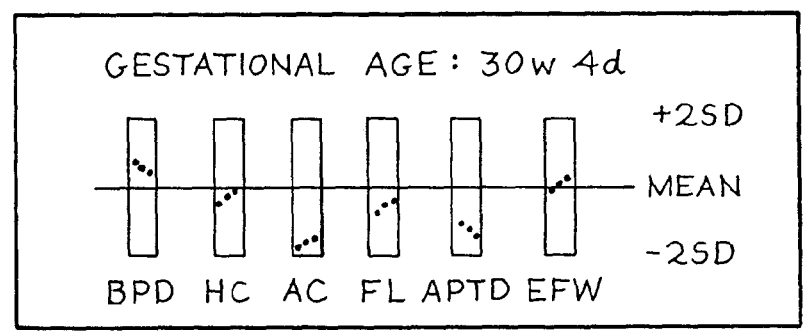
FIG. 4 is an illustration of a graphical display format of another embodiment.

It should be noted that different graphical display formats can be used to simultaneously display fetal growth data. For example, as shown in FIG. 4, the graphical format of FIG. 3 can be modified to allow the representation of fetal growth trends during the gestation by including data from multiple examinations throughout the gestation. In the graphical display format shown in FIG. 4, each dimension of fetal growth data contains a set of points representing data acquired throughout pregnancy, with the right-most point in each bar representing the data collected at the noted gestational age (30 weeks, 4 days).

Figure 5:
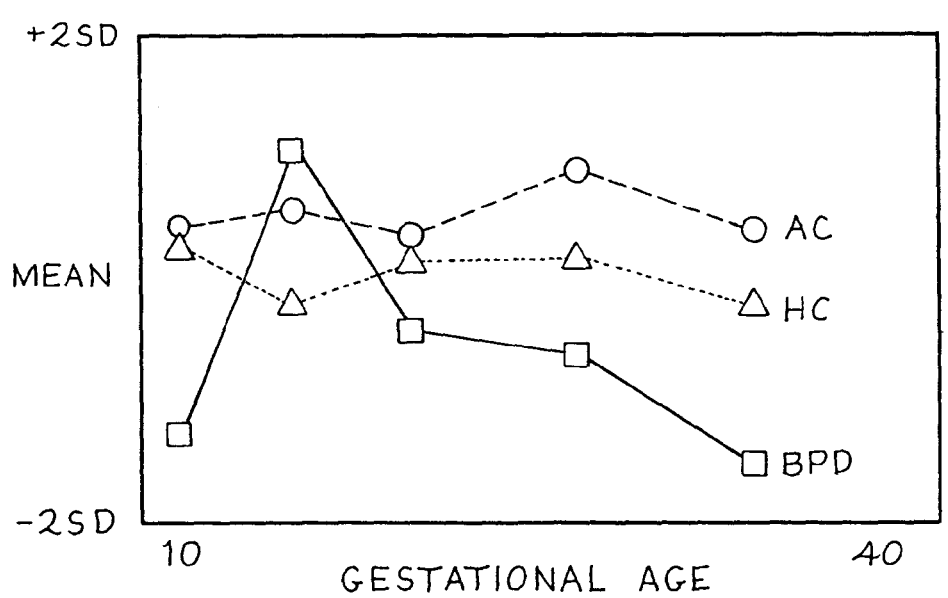
FIG. 5 is an illustration of a graphical display format of another embodiment.

FIG. 5 shows an alternate presentation of multidimensional fetal growth data that includes results from multiple examinations throughout gestation. In the graphical display format of FIG. 5, biparietal diameter, head circumference, and abdominal circumference are all plotted on the same graph. This graph illustrates expected value (mean) and standard deviations for each of the dimensions of fetal growth data versus gestational age. The "dots" (squares, triangles, and circles) on the graph indicate measurements obtained during the examination at various gestational ages, and each of the dimensions of fetal growth data is normalized with respect to the mean.

Figure 6:
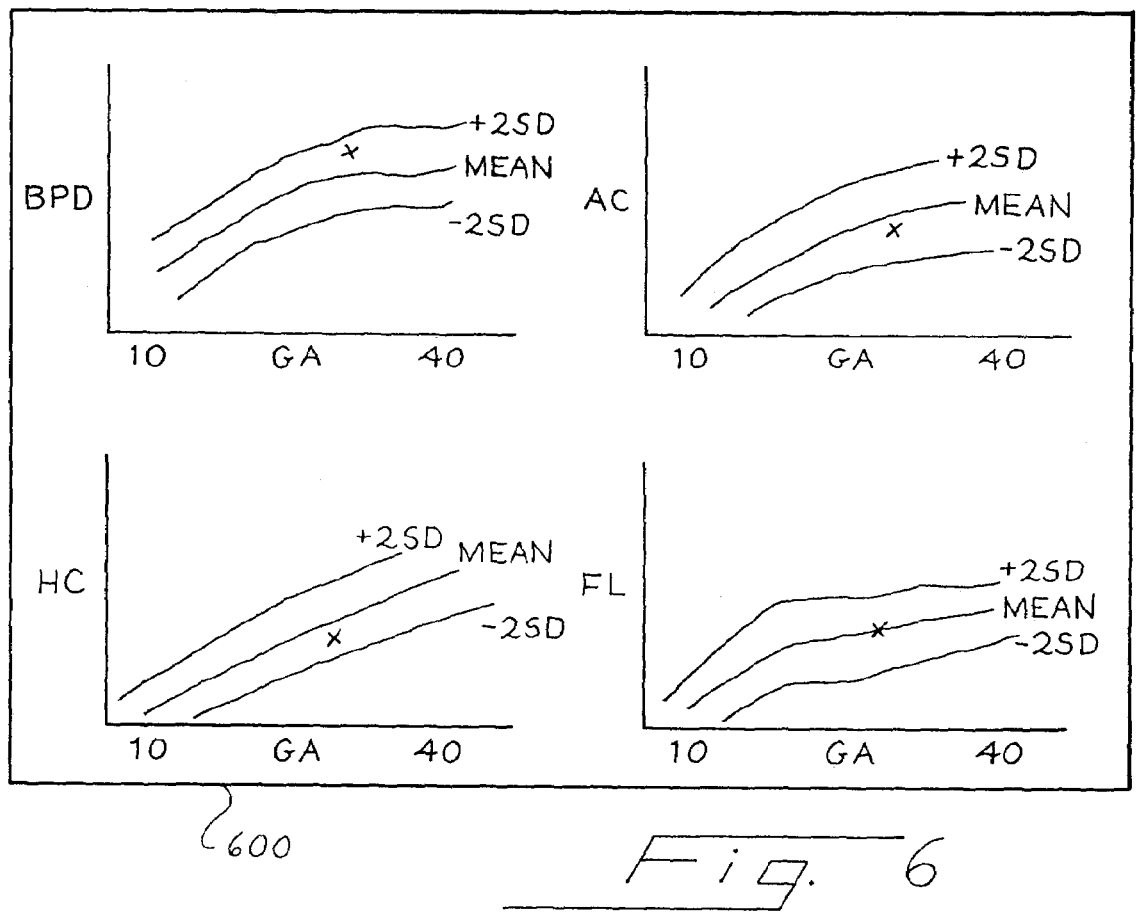
FIG. 6 is an illustration of a graphical display format of another embodiment

In the graphical display formats described above, multiple dimensions of fetal growth data were plotted on the same graph (i.e., different fetal growth data were overlapped onto the same display area). In an alternate graphical display format (shown in FIG. 6), multiple dimensions of fetal growth data are plotted on separate graphs (i.e., on separate display areas), while still being simultaneously displayed on a single display device 600. The various dimensions of fetal growth data can be normalized with respect to one another in this graphical display format.

In the embodiments described above, the fetal growth data was simultaneously displayed on the ultrasound system that created the image from which the fetal growth data was generated. In an alternate embodiment, the fetal growth data is simultaneously displayed on an image review system instead of on the ultrasound system that created the image from which the fetal growth data was generated. As used herein, the term "image review system" refers to any device other than the ultrasound system that created the image from which fetal growth data was generated that is capable of simultaneously displaying a plurality of fetal growth data. An image review system can be, for example, a general-purpose or specialized computer, a personal digital assistant (PDA), or another ultrasound system. The fetal growth data can be provided from an ultrasound system to the image review system via removable media (e.g., a magneto-optical disk), a network (e.g., a local area network in a hospital or the Internet), a wireless transmission, or any other suitable technique. In addition to simultaneously displaying fetal growth data, the image review system can perform other functions, such as displaying images, making measurements of anatomical structures shown in the images, generating fetal growth data based on the measurements, and creating medical reports.

Instead of simultaneously displaying fetal growth data, these embodiments can be used to simultaneously display non-obstetrics-based data (e.g., cardiology data). Data other than that generated from measurements taken of anatomy shown in a medical image can also be simultaneously displayed. The following is an example using time intensity curves.

Example Using Time Intensity Curves (TIC)

Another application of the general technique described above relates to time intensity curves (TIC) for cardiac contrast. TIC curves provide a way of determining how well heart tissue is functioning. In operation, a contrast agent is injected into the body. When the contrast agent has saturated the myocardium of the heart, for example, the ultrasound image of the myocardium appears very bright. At this time, a powerful ultrasonic pulse bursts the bubbles of which the contrast agent is comprised, causing the myocardium to appear dark. Now, as the heart continues to pump, contrast agent gradually fills the myocardium again. The speed with which this occurs can be plotted, producing a time-intensity curve. An individual TIC curve shows increasing intensity as a function of time. The rapidity with which the contrast agent refills the chamber is a measure of cardiac pathology (slow refill rate implies unhealthy heart muscle). Similar quantification of blood flow can also be done in the kidney or other perfused organs.

Several mathematical models for a TIC curve are available. One mathematical model for a TIC curve is:

$$A(1-e^{(-bt)})+C$$

where:

A, b, and C are constants t is time e is 2.7182818 . . .

^ is exponentiation

Another commonly-used function is $A*t*e^{(-alpha*t)}+C$. Both functions are discussed in Wei et al, "Basis for Detection of Stenosis Using Venous Administration of Microbubbles during Myocardial Contrast Echocardiography: Bolus or Continuous Infusion," Am Coll (Cardiol 32:252-60 (1998), which is hereby incorporated by reference. There are also measured parameters such as arrival time, time to peak, half-time of wash-in, and half-time of wash-out that can be used to describe the time-intensity curve.

The mathematical model "$A(1-e^{(-bt)})+C$" is an idealization expressing asymptotic increase of intensity from a minimum of C to a maximum of A+C. Given a TIC curve based on real ultrasound data, one can fit the above mathematical model, estimating the best-fit values for A, b, and C. A, b and the product A*b have physiological meaning and have been proposed as diagnostic of disease. See Linka et al., "Assessment of Transmural Distribution of Myocardial Perfusion with Contrast Echocardiography," Circulation 98:1912-1920 (1998), which is hereby incorporated by reference. The following discussion of displaying b values can equally be applied to the other parameters or their combination. The parameter "b," which is a measure of the rapidity of contrast agent refilling the chamber, has an average value to be found among a population of healthy hearts, and a standard deviation about that average value which might be found in a large population of healthy hearts. But, an unhealthy heart might display a value of b which differs from normal by, say, 2.5 standard deviations.

Some conventional ultrasound machines are able to produce and display multiple TIC curves corresponding to different locations of the heart wall. However, with this embodiment, rather than displaying the raw curves together, the above equation would be fitted to each of the individual curves, obtaining for each a value of "b." Then, the normalized b's are displayed on a single plot. Thus, the sonographer/physician sees, at a glance, not several curves overlying each other but rather a set of "b" values expressed in terms of how many standard deviations "b" is from normal. Not only is this much "cleaner" to the eye (a less busy plot), but it may also help indicate pathology more easily. In the case where one or two curves are particularly slow, then it may be easy to detect pathology using the traditional plotting method, because the slow curves stand out from the crowd. But if they are all slow, pathology may not be as obvious. However, the display of normalized "b's" will make the pathology obvious, because all the normalized "b's" will lie away from the "Normal" value.

Furthermore, it may be possible to develop theoretical models for the expected "b" for different parts of the heart muscle. In this case, each TIC measurement at a different location would be normalized using the expected "b" appropriate for that location, and again, the gamut of measurements would be simultaneously displayed in a single graphical display to determine which parts of the heart are diseased. Comparison of the multi-site TIC curves without such normalization could be significantly more difficult to properly interpret.

Figure 7:
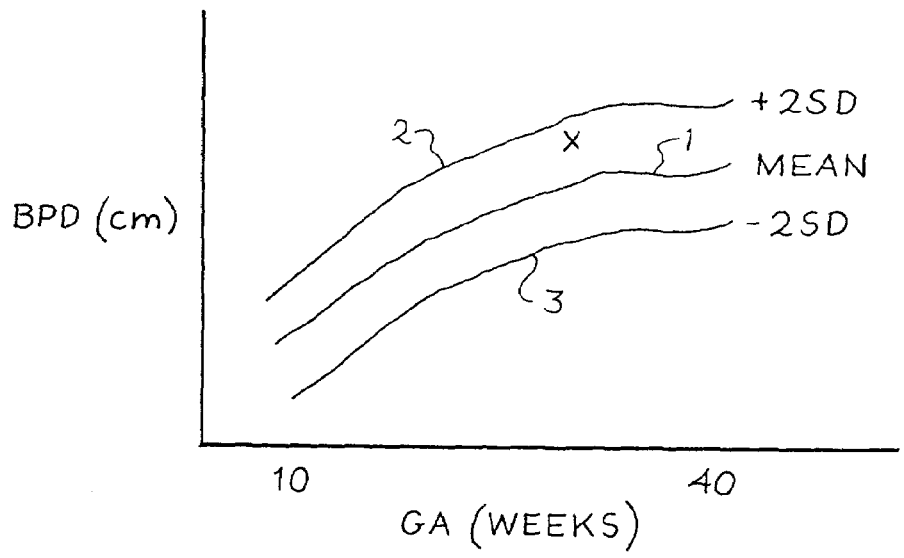
FIG. 7 is an illustration of a prior art growth curve.

In another embodiment, a time intensity curve is plotted on a graph similar to that shown in FIG. 7. Specifically, a single graph displays an ultrasound contrast time intensity curve of a study along with three curves. The first curve represents an expected ultrasound contrast time intensity curve, and the second and third curves represent a statistical variation of the expected ultrasound contrast time intensity curve.

Conclusion

While the embodiments have been described above in terms of ultrasound images, it should be noted that these embodiments can be used with any type of medical image. Examples of different types of medical images that can be used with these embodiments include, but are not limited to, images created with any of the following imaging modalities: computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

It is intended that the foregoing detailed description be understood as an illustration of selected forms that the invention can take and not as a definition of the invention. It is only the following claims, including all equivalents, that are intended to define the scope of this invention.

What is claimed is:

1. A method for simultaneously displaying relationships of measurements of features associated with a medical anatomic image of the interior of a single test subject, the method comprising:
   (a) providing a plurality of measurements of features associated with a medical anatomic image of the interior of a single test subject, each of the plurality of measurements corresponding to a respective measurement type;
   (b) associating each of the plurality of measurements with a reference specific to its measurement type;
   (c) for each of the plurality of measurements, creating a relationship between the measurement and the reference specific to its measurement type; and
   (d) simultaneously displaying at least two of the relationships created in (c) in a graphical display format, wherein an axis of the graphical display format is in a unitless measure of deviation.

2. The method of claim 1, wherein at least one of the plurality of measurements is associated with a time intensity curve.

3. The method of claim 2 wherein some of the measurements are referenced to values that are determined on the basis of the region or organ from which the data originates.

4. The method of claim 2, wherein at least one of the plurality of measurements is a parameter originating from fitting the time-intensity data with a known function.

5. The method of claim 1, wherein at least some of the plurality of measurements comprise different measurement types.

6. The method of claim 1, wherein at least one of the measurements comprises a quantification of a physiological attribute that appears in a medical image.

7. The method of claim 1, wherein at least one of the measurements comprises a quantification of a physiological attribute that is a calculation derived from raw imaging data.

8. The method of claim 1, wherein at least one of the measurements comprises a quantification of a physiological attribute that is available through an imaging system but is not data that is used to create a medical image.

9. The method of claim 1, wherein at least some of the relationships show a measure of deviation from a normal.

10. The method of claim 1, wherein (d) comprises displaying the at least two of the relationships in a single graph.

11. The method of claim 1, wherein (d) comprises displaying the at least two of the relationships in separate graphs.

12. The method of claim 1, wherein the medical anatomic image comprises an ultrasound image.

13. The method of claim 12 wherein the ultrasound image shows the movement of the contrast agent that has been injected in the patient being scanned.

14. The method of claim 1, wherein (d) is performed on a medical diagnostic imaging system.

15. The method of claim 1, wherein (d) is performed on an image review system.

16. The method of claim 1 wherein the image is enhanced by a contrast agent.

* * * * *